(12) United States Patent
Aamodt

(10) Patent No.: US 12,042,351 B2
(45) Date of Patent: *Jul. 23, 2024

(54) METHODS AND SYSTEMS FOR ORTHODONTIC TREATMENT PLANNING

(71) Applicant: CVSTOM Co., San Francisco, CA (US)

(72) Inventor: Kjeld A. Aamodt, San Francisco, CA (US)

(73) Assignee: CVSTOM Co., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,705

(22) Filed: May 2, 2023

(65) Prior Publication Data

US 2024/0033040 A1 Feb. 1, 2024

Related U.S. Application Data

(63) Continuation of application No. 17/146,053, filed on Jan. 11, 2021, now Pat. No. 11,678,955, which is a
(Continued)

(51) Int. Cl.
A61C 7/00 (2006.01)
A61C 9/00 (2006.01)
(Continued)

(52) U.S. Cl.
CPC .......... *A61C 7/002* (2013.01); *A61C 9/0006* (2013.01); *A61C 9/0053* (2013.01); *A61C 19/06* (2013.01);
(Continued)

(58) Field of Classification Search
CPC ..... A61C 7/002; A61C 9/0006; A61C 9/0053; A61C 19/06; G06T 7/0012; G06T 7/38;
(Continued)

(56) References Cited

U.S. PATENT DOCUMENTS 6,210,162 B1 4/2001 Chishti et al.
6,227,850 B1 5/2001 Chishti et al.
(Continued)

FOREIGN PATENT DOCUMENTS

CN 103405276 A 11/2013
CN 113040952 A 6/2021
(Continued)

OTHER PUBLICATIONS

Croci, C.S. et al. (2015). "Rotation axis of the maxillary molar and maximum tooth movement according to force direction," Braz. J. Oral. Sci. 14:130-134.
(Continued)

*Primary Examiner* — Molly Wilburn
(74) *Attorney, Agent, or Firm* — COOLEY LLP

(57) ABSTRACT

A method of orthodontic treatment planning for a patient includes receiving three-dimensional intraoral surface scan data of a dentition of the patient, receiving three-dimensional volumetric scan data of the dentition of the patient, and overlaying the intraoral surface scan data and the volumetric scan data to generate an integrated patient model comprising a root of at least one tooth having a longitudinal axis. The method further includes determining, for use in planning an orthodontic treatment, a center of rotation of the at least one tooth, wherein the center of rotation is defined as a point located a predetermined distance from a base of the root to an apex of the root along the longitudinal axis of the at least one tooth in the integrated patient model.

20 Claims, 16 Drawing Sheets

Related U.S. Application Data continuation of application No. 16/814,913, filed on Mar. 10, 2020, now Pat. No. 10,905,526.

(60) Provisional application No. 62/824,153, filed on Mar. 26, 2019.

(51) Int. Cl.
*A61C 19/06* (2006.01)
*G06T 7/00* (2017.01)
*G06T 7/38* (2017.01)
*G16H 30/20* (2018.01)
*G16H 30/40* (2018.01)

(52) U.S. Cl.
CPC ............. *G06T 7/0012* (2013.01); *G06T 7/38* (2017.01); *G16H 30/20* (2018.01); *G16H 30/40* (2018.01); *G06T 2207/10081* (2013.01); *G06T 2207/30036* (2013.01); *G06T 2207/30204* (2013.01)

(58) Field of Classification Search
CPC . G06T 2207/10081; G06T 2207/30036; G06T 2207/30204; G16H 30/20; G16H 30/40
See application file for complete search history.

(56) References Cited

U.S. PATENT DOCUMENTS

| | | |
|---|---|---|
| 6,371,761 B1 | 4/2002 | Cheang et al. |
| 6,386,878 B1 | 5/2002 | Pavlovskaia et al. |
| 6,394,801 B2 | 5/2002 | Chishti et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,602,070 B2 | 8/2003 | Miller et al. |
| 6,664,986 B1 | 12/2003 | Kopelman et al. |
| 6,688,886 B2 | 2/2004 | Hughes et al. |
| 6,726,478 B1 | 4/2004 | Isiderio et al. |
| 6,783,360 B2 | 8/2004 | Chishti |
| 6,786,721 B2 | 9/2004 | Chishti et al. |
| 6,792,952 B2 | 9/2004 | Mauro |
| 6,830,450 B2 | 12/2004 | Knopp et al. |
| 7,037,108 B2 | 5/2006 | Chishti et al. |
| 7,040,896 B2 | 5/2006 | Pavlovskaia et al. |
| 7,092,784 B1 | 8/2006 | Simkins |
| 7,273,367 B2 | 9/2007 | Hughes et al. |
| 7,275,930 B2 | 10/2007 | Taub et al. |
| 7,474,307 B2 | 1/2009 | Chishti et al. |
| 7,578,674 B2 | 8/2009 | Chishti et al. |
| 7,637,740 B2 | 12/2009 | Knopp |
| 7,904,308 B2 | 3/2011 | Arnone et al. |
| 7,970,627 B2 | 6/2011 | Kuo et al. |
| 7,987,099 B2 | 7/2011 | Kuo et al. |
| 8,038,444 B2 | 10/2011 | Kitching et al. |
| 8,095,383 B2 | 1/2012 | Arnone et al. |
| 8,099,305 B2 | 1/2012 | Kuo et al. |
| 8,260,591 B2 | 9/2012 | Kass et al. |
| 8,438,817 B2 | 5/2013 | Sankaran et al. |
| 8,807,999 B2 * | 8/2014 | Kuo .................. G16H 50/50 433/24 |
| 8,874,452 B2 | 10/2014 | Kuo |
| 8,896,592 B2 | 11/2014 | Boltunov et al. |
| 8,930,219 B2 | 1/2015 | Trosien et al. |
| 9,161,823 B2 | 10/2015 | Morton et al. |
| 9,375,300 B2 | 6/2016 | Matov et al. |
| 9,549,794 B2 | 1/2017 | Kopelman et al. |
| 9,615,901 B2 | 4/2017 | Babayoff et al. |
| 9,622,835 B2 * | 4/2017 | See .................. G06T 19/00 |
| 9,949,628 B2 | 4/2018 | Fisker et al. |
| 10,307,222 B2 | 6/2019 | Morton et al. |
| 10,482,192 B1 * | 11/2019 | Long .................. A61C 7/002 |
| 10,653,502 B2 | 5/2020 | Kuo |
| 10,657,662 B2 | 5/2020 | Lal et al. |
| 10,886,010 B2 | 1/2021 | Arnone et al. |
| 10,898,298 B1 | 1/2021 | Raslambekov |
| 10,905,526 B2 * | 2/2021 | Aamodt .................. G06T 7/38 |
| 11,678,955 B2 * | 6/2023 | Aamodt .............. A61C 9/0006 382/128 |
| 2004/0137400 A1 | 7/2004 | Chishti et al. |
| 2008/0020350 A1 * | 1/2008 | Matov .................. G06T 17/20 433/213 |
| 2012/0214121 A1 | 8/2012 | Greenberg |
| 2013/0151208 A1 | 6/2013 | Ito |
| 2014/0288894 A1 | 9/2014 | Chishti et al. |
| 2014/0329194 A1 * | 11/2014 | Sachdeva ............... A61C 7/002 433/24 |
| 2016/0074137 A1 | 3/2016 | Kuo et al. |
| 2016/0095670 A1 * | 4/2016 | Witte .................. A61C 7/002 433/24 |
| 2016/0302885 A1 | 10/2016 | Matov et al. |
| 2017/0100213 A1 | 4/2017 | Kuo et al. |
| 2018/0168776 A1 | 6/2018 | Webber |
| 2019/0029522 A1 | 1/2019 | Sato et al. |
| 2019/0175303 A1 * | 6/2019 | Akopov ................. A61C 7/002 |
| 2019/0244694 A1 | 8/2019 | Arnone et al. |
| 2019/0314117 A1 | 10/2019 | Morton et al. |
| 2020/0306010 A1 | 10/2020 | Aamodt |
| 2021/0082184 A1 * | 3/2021 | Claessen .................. G06N 3/08 |
| 2023/0121899 A1 | 4/2023 | Naumovets et al. |
| 2023/0122558 A1 | 4/2023 | Aamodt |

FOREIGN PATENT DOCUMENTS

| | | |
|---|---|---|
| EP | 3 015 086 A1 | 5/2016 |
| WO | WO-2020/104760 A2 | 5/2020 |
| WO | WO-2020/141366 A1 | 7/2020 |
| WO | WO-2020/197761 A1 | 10/2020 |

OTHER PUBLICATIONS

Extended European Search Report mailed on Dec. 2, 2022, for EP Application No. 20 779 248.2, filed on Mar. 10, 2020, 8 pages.
International Search Report mailed on Jun. 12, 2020, for PCT Application No. PCT/US2020/021921, filed on Mar. 10, 2020, 2 pages.
International Search Report mailed on Jan. 12, 2023, for PCT Application No. PCT/US2022/077717, filed on Oct. 6, 2022, 2 pages.
International Search Report mailed on Dec. 29, 2022, for PCT Application No. PCT/US2022/077719, filed on Oct. 6, 2022, 2 pages.
Low, K-L. (2004). "Linear Least-Squares Optimization for Point-to-Plane ICP Surface Registration," Technical Report TR04-004, Department of Computer Sciences, University of North Carolina at Chapel Hill, pp. 1-3.
Non-Final Office Action mailed on Jun. 24, 2020, for U.S. Appl. No. 16/814,913, filed Mar. 10, 2020, 10 pages.
Non-Final Office Action mailed on Aug. 18, 2022, for U.S. Appl. No. 17/146,053, filed Jan. 11, 2021, 21 pages.
Notice of Allowance mailed on Oct. 6, 2020, for U.S. Appl. No. 16/814,913, filed Mar. 10, 2020, 7 pages.
Notice of Allowance mailed on Jan. 17, 2023, for U.S. Appl. No. 17/146,053, filed Jan. 11, 2021, 11 pages.
Notice of Allowance mailed on Feb. 2, 2023, for U.S. Appl. No. 17/146,053, filed Jan. 11, 2021, 3 pages.
Notice of Allowance mailed on Apr. 28, 2023, for U.S. Appl. No. 17/146,053, filed Jan. 11, 2021, 10 pages.
Taubin, G. (1995). "Estimating the tensor of curvature of a surface from a polyhedral approximation," Proceedings of IEEE International Conference on Computer Vision, pp. 902-907, 7 total pages.
Written Opinion of the International Searching Authority mailed on Jun. 12, 2020, for PCT Application No. PCT/US2020/021921, filed on Mar. 10, 2020, 5 pages.
Written Opinion of the International Searching Authority mailed on Jan. 12, 2023, for PCT Application No. PCT/US2022/077717, filed on Oct. 6, 2022, 7 pages.

(56) References Cited

OTHER PUBLICATIONS

Written Opinion of the International Searching Authority mailed on Dec. 29, 2022, for PCT Application No. PCT/US2022/077719, filed on Oct. 6, 2022, 5 pages.

* cited by examiner

▲ = center of rotation

900

| | |
|---|---|
| Inclination | 12.42 deg |
| Angulation | 11.56 deg |
| Rotation | 47.29 deg |
| Left/Right | -2.95 mm |
| Forward/Backward | -3.17 mm |
| Extrusion/Intrusion | -0.64 mm |

METHODS AND SYSTEMS FOR ORTHODONTIC TREATMENT PLANNING

CROSS-REFERENCE TO RELATED APPLICATIONS

This application is a continuation of U.S. patent application Ser. No. 17/146,053 filed Jan. 11, 2021, now U.S. Pat. No. 11,678,955, which is a continuation of U.S. patent application Ser. No. 16/814,913 filed Mar. 10, 2020, now U.S. Pat. No. 10,905,526, which claims priority to U.S. Provisional Patent Application No. 62/824,153 filed Mar. 26, 2019, each of which is hereby incorporated in its entirety by this reference.

TECHNICAL FIELD

This invention relates generally to the field of orthodontic treatment planning.

BACKGROUND

Orthodontia is a specialty of dentistry that aims to correct a patient's teeth and jaws that are improperly positioned, such as for health and/or cosmetic reasons. Generally, orthodontic treatments leverage the application of external forces to cause the progressive movement of one or more teeth from their original improper positions to desired positions. One conventional orthodontic treatment involves bonding brackets to tooth surfaces and progressively adjusting wires coupled to the brackets, in order to urge teeth toward desired positions and orientations. Another conventional orthodontic treatment involves the wearing of clear aligner trays with tooth-receiving cavities, to progressively move teeth toward final positions and orientations.

Planning such orthodontic treatments include obtaining a physical model and/or digital model of a patient's dentition and using such models to generate proposed treatment paths for each tooth to be moved. For example, a physical model of a patient's dentition can be obtained through a mold impression, while a digital model can be obtained by scanning the patient's dentition (and/or a physical model of the patient's dentition) with a scanning device. However, such modeling methods are limited in the amount of patient information that may be obtained, thereby leading to inaccurate treatment plans and longer total treatment times. Thus, there is a need for improved methods and systems for orthodontic treatment planning.

SUMMARY

Generally, a method of orthodontic treatment planning for a patient includes receiving three-dimensional intraoral surface scan data of a dentition of the patient, receiving three-dimensional volumetric scan data of the dentition; overlaying the intraoral surface scan data and the volumetric scan data to generate an integrated patient model comprising a root of at least one tooth having a longitudinal axis and determining, for use in planning an orthodontic treatment, a center of rotation of the at least one tooth, wherein the center of rotation is defined as a point located a predetermined distance from a base of the root to an apex of the root along the longitudinal axis of the at least one tooth in the integrated patient model. For example, the determined center of rotation of the at least one tooth may be defined as a point located between about one-third and about one-half (e.g., about one-third) of the distance between the base of the root to the apex of the root along the longitudinal axis. The root may, for example, be an anatomical root (e.g., extending from the dentinoenamel junction (DEJ) of the tooth to the root apex of the tooth), or a functional root (e.g., extending from the crestal bone height for the tooth to the root apex of the tooth). In some variations, the intraoral surface scan data may include optical color scan data, and/or the volumetric scan data may include X-ray scan data such as CBCT.

In some variations, overlaying the intraoral surface scan data and the volumetric scan data includes registering the intraoral surface scan data with the volumetric scan data. For example, such registration may align one or more fiducials (e.g., anatomical landmarks, artificial fiducials such as radiopaque markers, etc.). In some variations, the three-dimensional volumetric scan data includes data for the dentition and the craniofacial structure of the patient.

Generally, a system for orthodontic treatment planning for a patient includes at least one memory device configured to receive and store three-dimensional intraoral surface scan data of a dentition of the patient, and three-dimensional volumetric scan data of the dentition. The system may further include at least one processor configured to overlay the intraoral surface scan data and the volumetric scan data to generate an integrated patient model comprising a root of at least one tooth having a longitudinal axis. The system may include one or more displays configured to display the integrated patient model and/or a user interface for navigating the integrated patient model. The processor may further be configured to determine, for use in planning an orthodontic treatment, a center of rotation of the at least one tooth, wherein the center of rotation is defined as a point located a predetermined distance from a base of the root to an apex of the root along the longitudinal axis of the at least one tooth in the integrated patient model. For example, the determined center of rotation of the at least one tooth may be defined as a point located between about one-third and about one-half (e.g., about one-third) of the distance between the base of the root to the apex of the root along the longitudinal axis. The root may, for example, be an anatomical root (e.g., extending from the dentinoenamel junction (DEJ) of the tooth to the root apex of the tooth), or a functional root (e.g., extending from the crestal bone height for the tooth to the root apex of the tooth). In some variations, the intraoral surface scan data may include optical color scan data, and/or the volumetric scan data may include X-ray scan data such as CBCT.

In some variations, the processor may be configured to register the intraoral surface scan data and the volumetric scan data when overlaying the intraoral surface scan data and the volumetric scan data. For example, such registration may align one or more fiducials (e.g., anatomical landmarks, artificial fiducials such as radiopaque markers, etc.). In some variations, the three-dimensional volumetric scan data includes data for the dentition and the craniofacial structure of the patient.

Generally, a method of orthodontic treatment planning for a patient includes receiving three-dimensional intraoral surface scan data of a dentition of the patient, receiving three-dimensional volumetric scan data of the dentition and a craniofacial structure of the patient; overlaying the intraoral surface scan data and the volumetric scan data to generate an integrated patient model comprising a root of at least one tooth having a longitudinal axis, automatically separating the root of the at least one tooth from portions of the integrated patient model surrounding the foot, and determining, for use in planning an orthodontic treatment, a center of rotation of the at least one tooth. In some variations, the intraoral surface scan data may include optical color scan data, and/or the volumetric scan data may include X-ray scan data such as CBCT.

In some variations, the center of rotation of at least one tooth may be determined automatically (e.g., by a computing device) based on the integrated patient model resulting from the overlay of scan data. For example, the process of determining the center of rotation may involve automatically separating (in the integrated patient model) the root of at least one tooth, the periodontal ligaments associated with the at least one tooth, and/or the bone surrounding the at least one tooth, based at least in part on voxel density. For example, in some variations, automatically separating the root of the at least one tooth may include determining the voxel density of the at least one tooth in the integrated patient model and comparing the determined voxel density with a predetermined threshold voxel density for the at least one tooth. As another example, automatically separating the root of the at least one tooth may include determining a first voxel density of the at least one tooth in the integrated patient model, determining a second voxel density of at least one of: one or more periodontal ligaments associated with the at least one tooth in the integrated patient model, and the bone surrounding the at least one tooth in the integrated patient model, and comparing the difference between the first and second voxel densities to a predetermined threshold difference.

Furthermore, determining the center of rotation may further include determining volume of the at least one tooth and determining a longitudinal axis of the at least one tooth in the integrated patient model. In some variations, the determined center of rotation of the at least one tooth may be defined as a point located between about one-third and about one-half (e.g., about one-third) of the distance from the base of the root to the apex of the root along the longitudinal axis. The center of rotation may then be used in planning an orthodontic treatment, such as orthodontic treatment via a plurality of aligner trays with tooth-receiving cavities, where each aligner tray corresponds to a respective tooth arrangement such that the series of aligner trays progressively move teeth in treatment paths in accordance with their centers of rotation for natural movement.

Generally, a system for orthodontic treatment planning for a patient includes at least one memory device configured to receive and store three-dimensional intraoral surface scan data of a dentition of the patient, and three-dimensional volumetric scan data of the dentition and a craniofacial structure of the patient. The system may further include at least one processor configured to overlay the intraoral surface scan data and the volumetric scan data to generate an integrated patient model comprising a root of at least one tooth having a longitudinal axis. The system may include one or more displays configured to display the integrated patient model and/or a user interface for navigating the integrated patient model. The processor may further be configured to automatically separate the root of the at least one tooth from portions of the integrated patient model surrounding the root, and to determine, for use in planning an orthodontic treatment, a center of rotation of the at least one tooth. In some variations, the intraoral surface scan data may include optical color scan data, and/or the volumetric scan data may include X-ray scan data such as CBCT.

In some variations, the center of rotation of at least one tooth may be determined automatically (e.g., by a computing device) based on the integrated patient model resulting from the overlay of scan data. For example, the processor may be configured to determine the center of rotation of at least one tooth at least in part by automatically separating (in the integrated patient model) the root of the at least one tooth, the periodontal ligaments associated with the at least one tooth, and/or the bone surrounding the at least one tooth, based at least in part on voxel density. Furthermore, the processor may be configured to automatically determine volume of the at least one tooth and determine the longitudinal axis of the at least one tooth in the integrated patient model. In some variations, the determined center of rotation of the at least one tooth may be defined as a point located between about one-third and about one-half (e.g., about one-third) of the distance from the base of the root to the apex of the root along the longitudinal axis. The center of rotation may then be used in planning an orthodontic treatment, such as orthodontic treatment via a plurality of aligner trays with tooth-receiving cavities, where each aligner tray corresponds to a respective tooth arrangement such that the series of aligner trays progressively move teeth in treatment paths in accordance with their centers of rotation for natural movement.

DETAILED DESCRIPTION

Non-limiting examples of various aspects and variations of the invention are described herein and illustrated in the accompanying drawings.

Described herein are methods and systems for increasing precision of an orthodontic treatment plan to move teeth. Specifically, the methods and systems described herein enable determination of root orientation of a tooth and a corrected center of rotation of the tooth. The center of rotation of the tooth may then be used in treatment planning to base a treatment path along a natural axis of movement, thereby achieving significant clinical benefit such as by reducing total treatment time.

Methods for Orthodontic Treatment Planning

Figure 1:
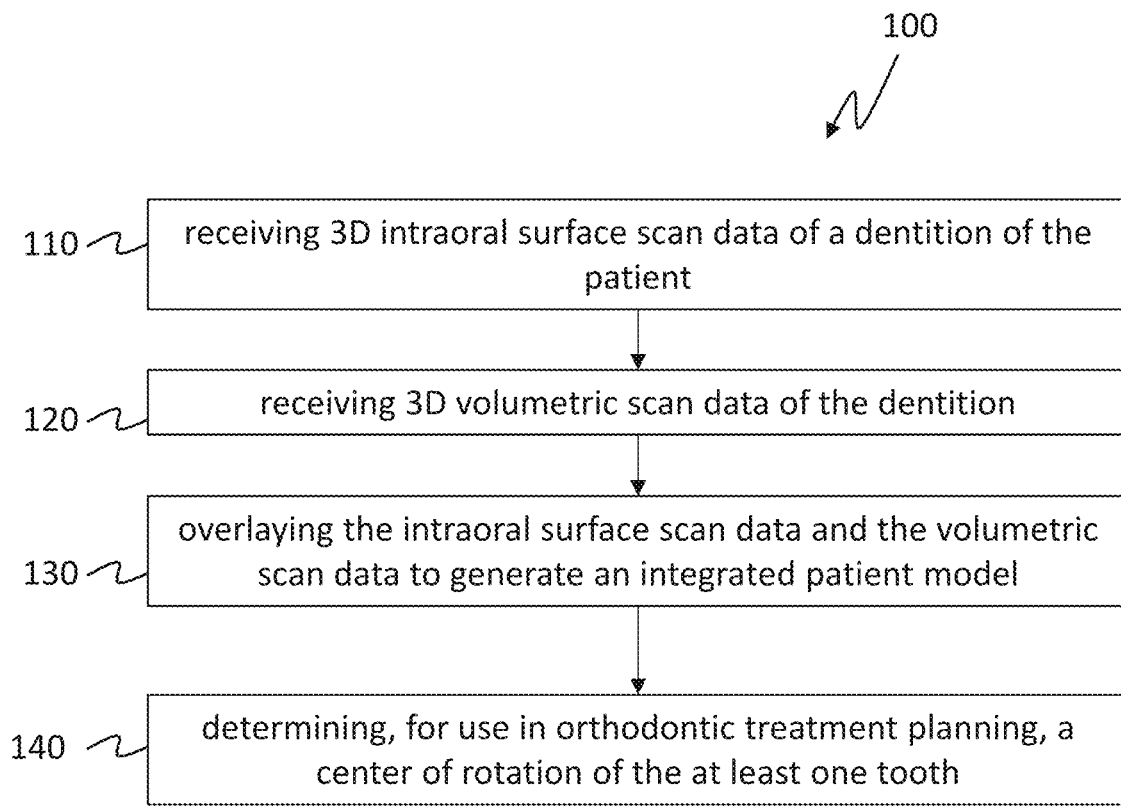
FIG. 1 is a schematic illustration depicting one variation of a method for orthodontic treatment planning.

Generally, as shown in FIG. 1, in some variations, a method 100 of orthodontic treatment planning for a patient includes receiving three-dimensional intraoral surface scan data of a dentition of the patient 110, receiving three-dimensional volumetric scan data of the dentition of the patient 120, overlaying the intraoral surface scan data and the volumetric scan data to generate an integrated patient model 130; and determining, for use in planning an orthodontic treatment, a center of rotation of the at least one tooth 140. In some variations, the integrated patient model includes a root of at least one tooth having a longitudinal axis, and the center of rotation may be defined as a point located a predetermined distance from a base of the root to an apex of the root along the longitudinal axis of the at least one tooth in the integrated patient model.

Scan Data

Figure 2:
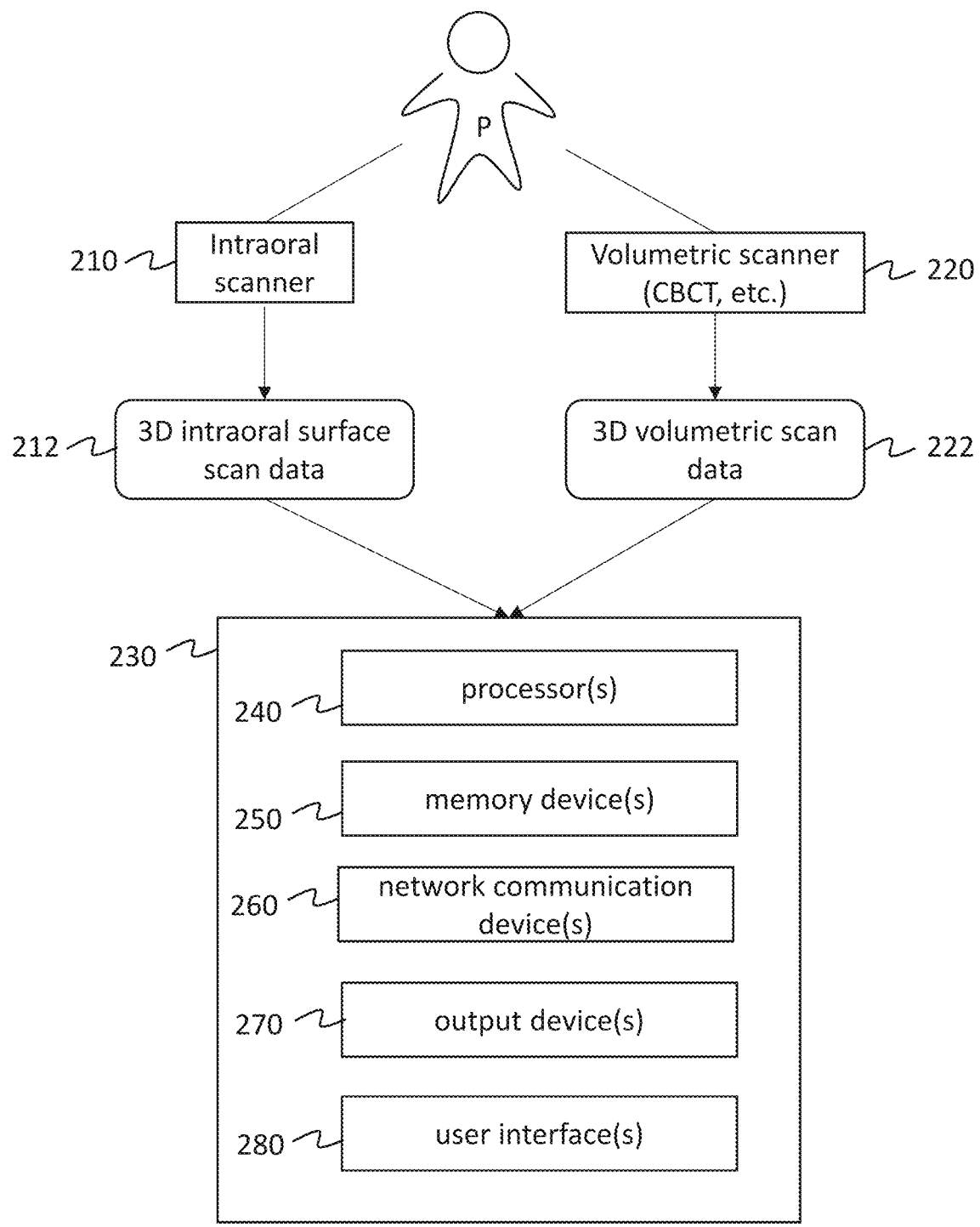
FIG. 2 is a schematic illustration depicting a one variation of a system for orthodontic treatment planning.

As shown in the schematic of FIG. 2, a first scan data set (e.g., intraoral surface scan data 212) and a second scan data set (e.g., volumetric scan data 222) may be generated by one or more scanning devices configured to obtain anatomical imaging data for a patient P. For example, an intraoral scanning device 210 may be used by a practitioner or other user to obtain image data (e.g., optical color scan data) representative of external surfaces of a patient's dentition (e.g., teeth crowns, gingiva, etc.). The intraoral scanning device may, for example, be a handheld scanner that emits light toward the patient's dentition as the scanner is manipulated inside the mouth of the patient. The emitted light reflects off surfaces of the patient's dentition, and the reflected light is captured by the intraoral scanner and subsequently analyzed to transform the reflected light data into surface imaging data. An exemplary intraoral scanner suitable for use in obtaining three-dimensional intraoral surface scan data 212 is the CS 3600 intraoral scanner available from CARESTREAM DENTAL LLC (Atlanta, Georgia, USA). However, any suitable intraoral scanners may be used to obtain such intraoral surface scan data 212.

Generally, the digitized surfaces of the patient's dentition obtained from the intraoral surface scan may be used to create one or more patient-customized orthodontic appliances (e.g., using computer-aided design and computer-aided manufacturing (CAD/CAM) technology), which may, for example, be used to apply forces to teeth and induce controlled orthodontic tooth movement (OTM) Accurate surface scan data of a patient's teeth enable such appliances to have a predictably intimate fit to the unique curvatures of the teeth. Moreover, precise manipulation of accurate intraoral surface scan data allows the creation of orthodontic appliances to induce effective OTM.

Figure 4:
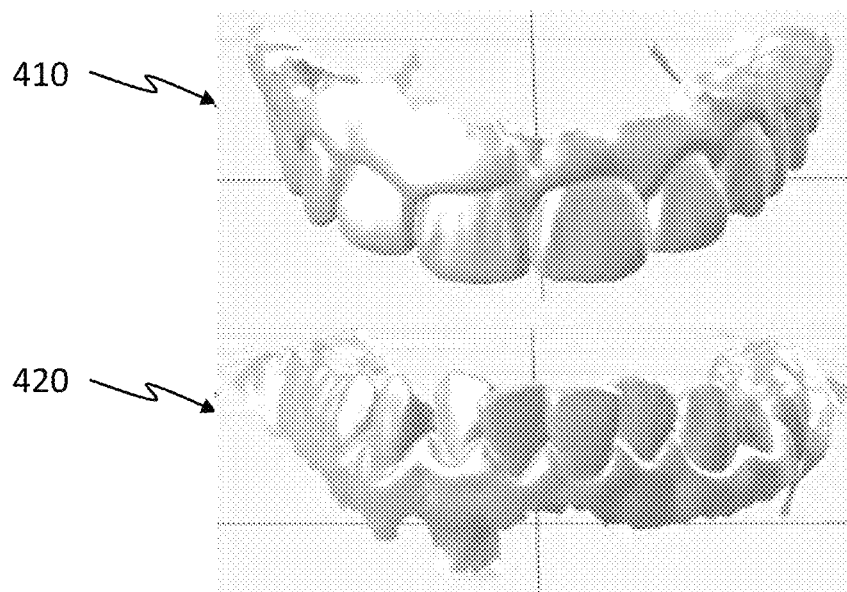
FIG. 4 depicts exemplary raw surface scan images based on intraoral surface scan data of a patient's dentition.
Figure 5:
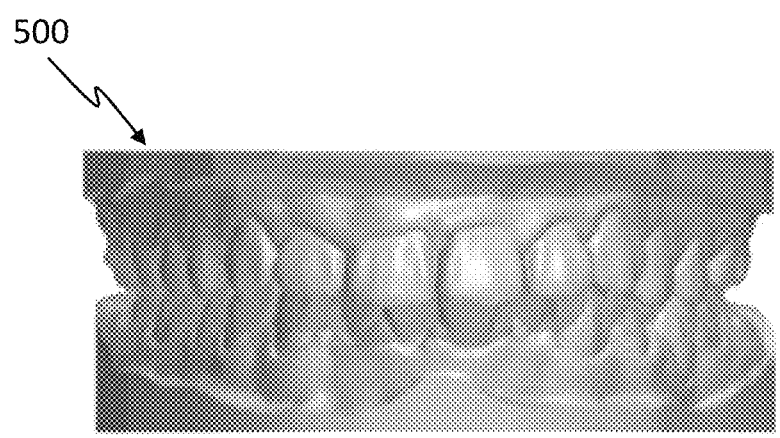
FIG. 5 depicts an exemplary prepared surface scan model based on the raw surface scan images depicted in FIG. 4.

FIG. 4 illustrates exemplary raw surface scan images based on intraoral surface scan data for a patient's upper dentition 410 and lower dentition 420. As shown in FIG. 4, while intraoral surface scan data may provide information about the external form of the tooth crowns and at least a portion of gingiva, the intraoral surface scan data does not supply direct information about certain other tooth structures such as length and size of the underlying tooth roots and bone. Furthermore, the raw surface scan data may be manipulated into a prepared surface scan model such as the model 500 shown in FIG. 5. For example, the scan images may be trimmed to include only relevant scan data, and/or placed onto a template jaw base model, etc.

The volumetric scan data 222 may be obtained by a volumetric scanner 220. In some variations, the volumetric scanner may provide three-dimensional X-ray imaging (e.g., cone-beam computed tomography (CBCT)) of dentition (e.g., crowns, gingiva, root structures) and craniofacial features (e.g., bone). Specifically, the volumetric scanner may be configured to provide detailed information regarding each tooth's root orientation. An exemplary CBCT X-ray scanner suitable for use in obtaining three-dimensional volumetric scan data 222 is the RAYSCAN a imaging device available from RAY COMPANY (RAY AMERICA, Inc., Fort Lee, New Jersey, USA). However, any suitable extraoral scanners providing volumetric information of dentition and craniofacial features may be used to obtain the volumetric scan data 222.

Figure 6:
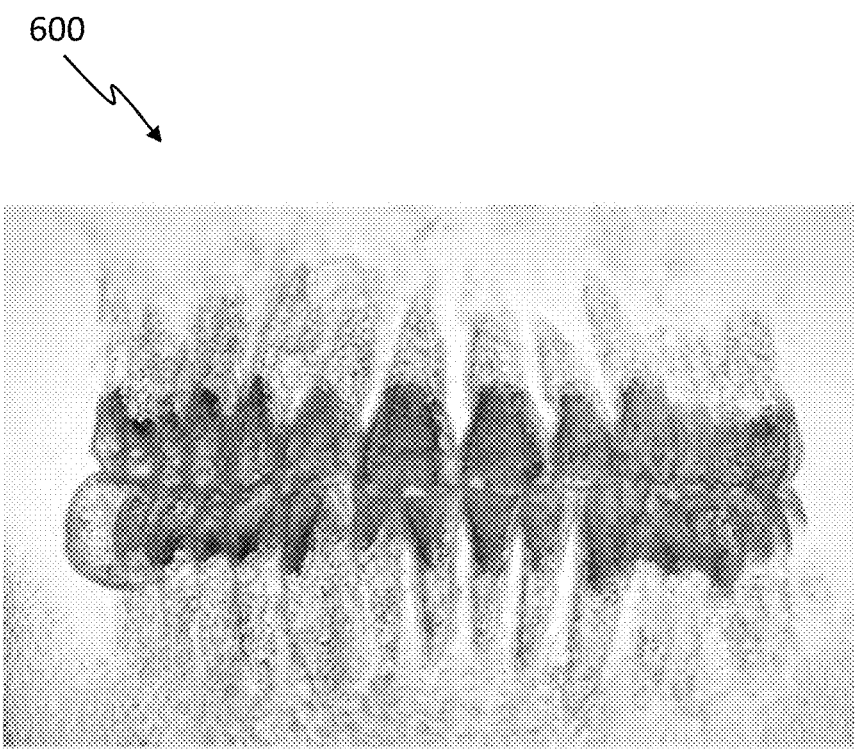
FIG. 6 depicts an exemplary volumetric scan image of a patient's dentition.

Generally, the volumetric scan data obtained from an ionizing or non-ionizing volumetric scanner may be used to identify patient anatomical features such as bone structures, crowns and roots of teeth, and/or pathology of the craniofacial region, as well as to measure or otherwise quantify other patient characteristics such as airway volume, facial phenotype, and/or malocclusion of the jaws. For example, as shown in FIG. 6 depicting an exemplary volumetric scan image 600, the volumetric scan data may provide the volume, length, and/or morphology of tooth roots. This information relating to tooth roots may improve the modeling of orthodontic tooth movement by, for example, allowing the specification of each tooth's actual center of resistance and long axis for rotation within the patient's jawbone, as further described below.

Model Segmentation

Figure 7:
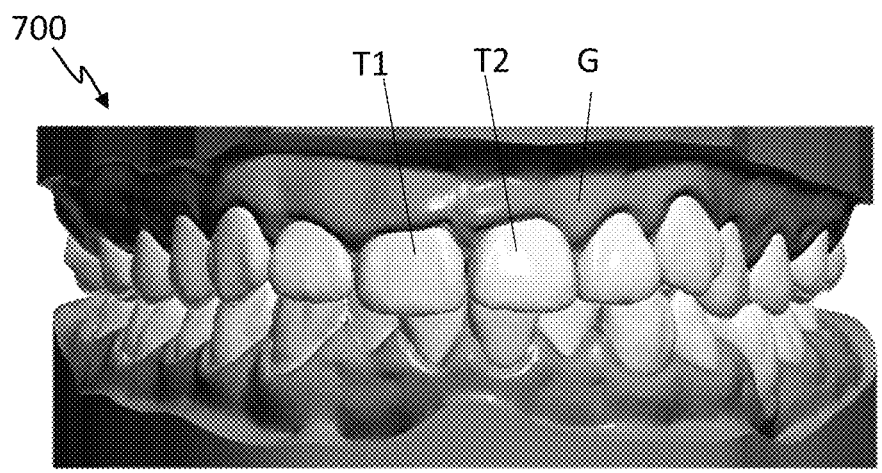
FIG. 7 depicts an exemplary segmented intraoral surface scan model of a patient's dentition.
Figure 8:
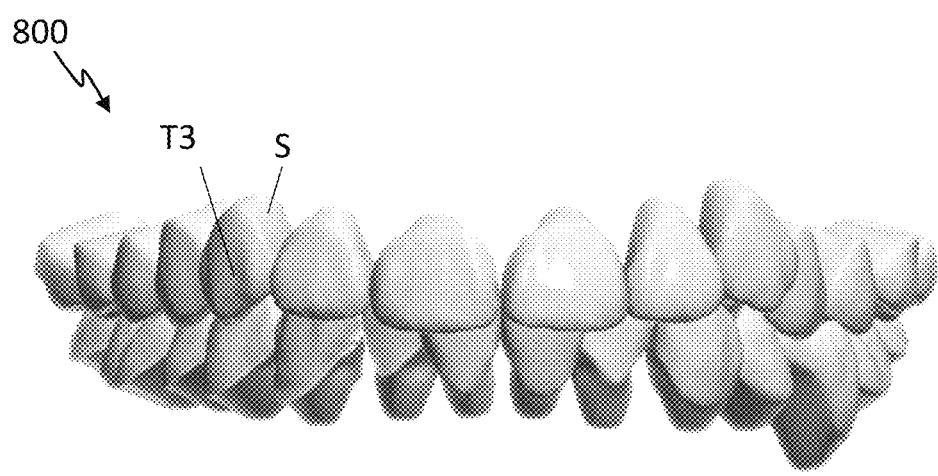
FIG. 8 depicts a segmented and capped intraoral surface scan model of a patient's dentition.

In some variations, discrete portions of a model corresponding to the surface scan data and/or a model corresponding to the volumetric scan data may be identified in a model segmentation process. For example, different portions of a model, where the different portions correspond to different anatomical features, may be segmented. For example, different teeth in the model may be segmented in order to enable independent selection, viewing, and/or manipulation of each tooth in isolation. In some variations, at least the root structure of at least one tooth in the model may be separated (as a discrete, identifiable volume) from the rest of the model. Additionally or alternatively, the model may be segmented to separate other anatomical features such as the crown of each tooth, gingiva, periodontal ligament(s), and bone. For example, FIG. 7 depicts a segmented model 700 corresponding to intraoral surface scan data, in which individual teeth (e.g., T1 and T2) are segmented as separate structures, and the teeth are further segmented with respect to gingiva (G). In some variations, model segmentation may further include isolating one or more anatomical features, such as to enable individual selection and display of an isolated feature, for example. For example, FIG. 8 depicts a portion of an intraoral surface scan model including tooth crowns that are segmented and "capped" with a smooth surface (e.g., tooth T3 is segmented and capped with a surface S). Similarly, other portions of the intraoral surface scan model (gingiva, tooth roots, etc.) and/or volumetric scan model may be segmented and capped for display and/or analysis. In some variations, the model corresponding to the surface scan data and the model corresponding to the volumetric scan data may each be individually and separately segmented and/or capped. Alternatively, in some variations, segmentation and/or capping may alternatively be performed on an integrated patient model obtained by previously overlaying the surface scan data and the volumetric scan data as described below.

In some variations, model segmentation may be performed with manual input. For example, similar to that described above, markers may be placed on the model by a user through the user interface to designate one or more anatomical features for defining segmentation boundaries, such as a plane or other surface between two teeth, between a tooth and gingiva, or between a tooth crown and a tooth root. Alternatively, markers may be placed on the integrated patient model after overlaying the scan data in the overlaying process described below. Once placed, the markers may be adjusted by the user. In other variations, markers denoting segmentation boundaries may be automatically suggested and placed by a software algorithm (and may be confirmed and/or adjusted based on user manual input). For example, proposed segmentation boundaries may be automatically defined based on color pixel data in the surface scan data and/or overlaid integrated patient model. As an illustrative example, a threshold color channel intensity change between adjacent pixels in the surface scan data and/or overlaid integrated patient model may indicate a transition between a light-colored tooth and a darker-colored or pink gingiva.

Furthermore, in some variations, model segmentation may be automatically performed based at least in part on voxel density of various voxels in the volumetric scan model (and/or integrated patient model). Different kinds of patient tissue will be represented with different voxel density in the volumetric scan data, as the result of the differing radiopacity of different kinds of tissue. For example, bones have relatively higher radiopacity than gingiva, and therefore will be represented with greater voxel density than gingiva in a CBCT scan. As another example, tooth enamel and root dentin have a higher radiopacity than their surrounding alveolar bone, and will be represented with greater voxel density than surrounding bone in the volumetric scan data. Accordingly, in some variations, different regions in the integrated patient model may be automatically identifiable by monitoring threshold changes in voxel density across neighboring voxels in the integrated patient model, thereby aiding segmentation.

In some variations, partial or full segmentation of both the surface scan model and the volumetric scan model may be performed prior to overlaying the models to form an integrated patient model. In some variations, partial or full segmentation of the integrated patient model may be performed after overlaying (at least partially) unsegmented surface scan and volumetric scan models. In yet other variations, either the surface scan model or the volume scan model may be segmented after their overlay, based at least in part on alignment information derived from the integrated patient model. For example, a pre-segmented intraoral surface scan model may have data about tooth-tooth boundaries and/or tooth-gingiva boundaries, and may be utilized to "seed" or otherwise inform the identification and segmentation of the aligned volumetric data for the interface between the tooth root and bone. For example, the gingival margin of a tooth may be extrapolated toward the tooth's root apex, in that the density value of the voxels around the tooth margin identified in the intraoral surface scan may seed the identification and growth of that tooth's associated root along the root-bone boundary.

Overlaying Data

Figure 9:
FIG. 9 depicts an exemplary integrated patient model incorporating intraoral surface scan data and volumetric scan data for a patient's dentition.

Overlaying the intraoral surface scan data and the volumetric scan data 130 functions to generate a high-precision, integrated patient model including useful information from the surface scan data and the volumetric scan data, such as root orientation, tooth volumes, etc. For example, FIG. 9 depicts an illustrative integrated patient model that includes an overlay of aligned surface scan and volumetric scan models. Generally, the scan data may be imported into a software application on a computing device for display in a user interface. Software instructions stored on a machine-readable storage medium (as described in further detail below) may enable display and manipulation of the intraoral surface scan data and the volumetric scan data on the computing device.

The software instructions may, in some variations, enable registration of the intraoral surface scan data with the volumetric scan data such that both sets of scan data are aligned. The registered intraoral surface scan data and volumetric scan data may share a common coordinate system, such that a resulting integrated patient model may be manipulated within the common coordinate system. Registration of the scan data may include, for example, alignment of one or more anatomical landmarks (e.g., visible crown features) and/or fiducials (e.g., radiopaque and optically visible markers in the patient's mouth and/or on the patient's dental features). Generally, the digitized surface scan and volumetric scan models may be aligned by a computational best-fit alignment algorithm, which may, for example, provide for six degrees of freedom in adjustment and scaling as needed. The best-fit algorithm may be performed separately once for the upper teeth, and once for the lower teeth.

One or both of the intraoral surface scan data and the volumetric scan data may be rescalable and/or rotatable to better facilitate the alignment and overlay of the scan data. For example, the software instructions may enable display of one or more handle icons associated with "grab points" on the scan data. Such handle icons may be manipulated (e.g., with a "click and drag" function) with a user input device such as a mouse or a touch screen, in order to rescale and/or rotate the scan data. Furthermore, the software instructions may enable selected portions of the intraoral surface scan data and/or volumetric scan data to be isolated via cropping or other similar image editing functionality.

In some variations, the overlaying of the intraoral surface scan data and the volumetric scan data may be performed manually. For example, user input may manipulate one or both sets of scan data until the scan data are scaled and/or aligned appropriately. As another example, a user may select a minimum number of points per jaw in corresponding locations on the surface scan model and the volumetric scan model (e.g., three or more on each jaw, per model) as key points, and align the respective sets of key points on the models in order to overlay them into an integrated patient model. In some variations, the overlaying of the intraoral surface scan data and the volumetric scan data may be performed automatically with suitable machine vision techniques (e.g., edge detection, corner finding, etc.). In yet other variations, the overlaying of the intraoral surface scan data and the volumetric scan data may be performed semi-automatically utilizing both manual and algorithmic techniques. For example, a user may manually indicate corresponding locations on the multiple images of scan data with virtual markers (e.g., placed on distinctive malocclusions, on key points such as along the interproximal margin, along various crown outlines or gingiva boundaries, etc.), and software instructions may be executed to automatically scale the images as necessary and/or align the corresponding virtual markers to produce the overlaid set of scan data (e.g., using a suitable computational best-fit algorithm). The results of such automatic or semi-automatic operation may be further adjusted with manual input and/or require manual input to indicate approval of the automatically or semi-automatically generated integrated patient model.

After at least a portion of the intraoral surface scan data and at least a portion of the volumetric scan data are overlaid to generate an integrated patient model, the integrated patient model may be displayed in a user interface on the computing device for further use during diagnosis and/or treatment planning. For example, the integrated patient model may be rotated for viewing in different perspectives, displayed with suitable cut-away or cross-sectional views.

In some variations, the intraoral surface scan data and the volumetric surface scan data may capture different states of the patient's dentition. For example, the intraoral surface scan and the volumetric scan may have been performed at different times, and the patient's structures (e.g., teeth, gingiva, etc.) may have moved through natural physiologic processes such as growth and remodeling, and/or by induced processes like orthodontic treatment. In these variations, such as if one or more teeth and/or jaws have moved, digital alignment of surface scan and volumetric scan models may be executed on a tooth-by-tooth basis to help ensure accurate crown-to-root alignment among the models. Furthermore, it may be helpful in some variations to segment the teeth of one of the two data sets (surface scan or volumetric scan) prior to overlay, in order to help with crown-to-root alignment.

Once registration or alignment of the surface scan and volumetric scan models is obtained, the crown morphology supplied by any new (subsequent) surface scan may also be used to infer the new position of the roots using the actual root morphology from previous integrated patient model(s).

Determining Center of Rotation

At least one tooth in the integrated patient model may be analyzed to determine its center of rotation (e.g., centroid), which may be used in treatment planning to derive a natural axis of movement for the tooth, thereby advantageously shortening total treatment time and improving accuracy of treatment. Generally, in some variations, the center of rotation may be determined for every tooth that is planned to undergo treatment.

In some variations, the center of rotation of a tooth in the integrated patient model may be defined as a point located a predetermined distance along a longitudinal axis of the tooth. In these variations, determining the center of rotation of a tooth may include determining the longitudinal axis of the tooth. The longitudinal axis of the tooth may be defined manually based on user input (e.g., by placement of one or more markers on the integrated patient model for that tooth). For example, a user may visually inspect the tooth in at least one perspective view of the integrated patient model, and mark or adjust a central line that runs axially along the tooth (including crown and root). One exemplary method of manually identifying the longitudinal axis of the tooth includes marking a first line that generally divides the tooth into two equally volumetric longitudinal halves when viewed from a first side perspective, and marking a second line that generally divides the tooth into two equally volumetric longitudinal halves when viewed from a second side perspective. The first and second lines may be extended into planes, and the longitudinal axis of the tooth may be defined as the line of intersection between the two planes. Another exemplary method of manually identifying the longitudinal axis of the tooth includes marking a top central point of the tooth when viewed from a top perspective, and marking a bottom central point of the tooth when viewed from a bottom perspective. In this example, the longitudinal axis of the tooth may be defined as the line extending between the top central point and bottom central point of the tooth.

Following determination of the longitudinal axis of the tooth, the center of rotation of the tooth may be determined as a point located a predetermined distance along the longitudinal axis. In some variations, for example, the center of rotation may be defined as a predetermined distance from a base of the tooth root to an apex of the tooth root along a longitudinal axis of the tooth. In an exemplary variation, the center of rotation may be determined to be at a point about one-third of the tooth length measured from a base of the tooth root to an apex of the tooth root along the longitudinal axis of the tooth.

Figure 3:
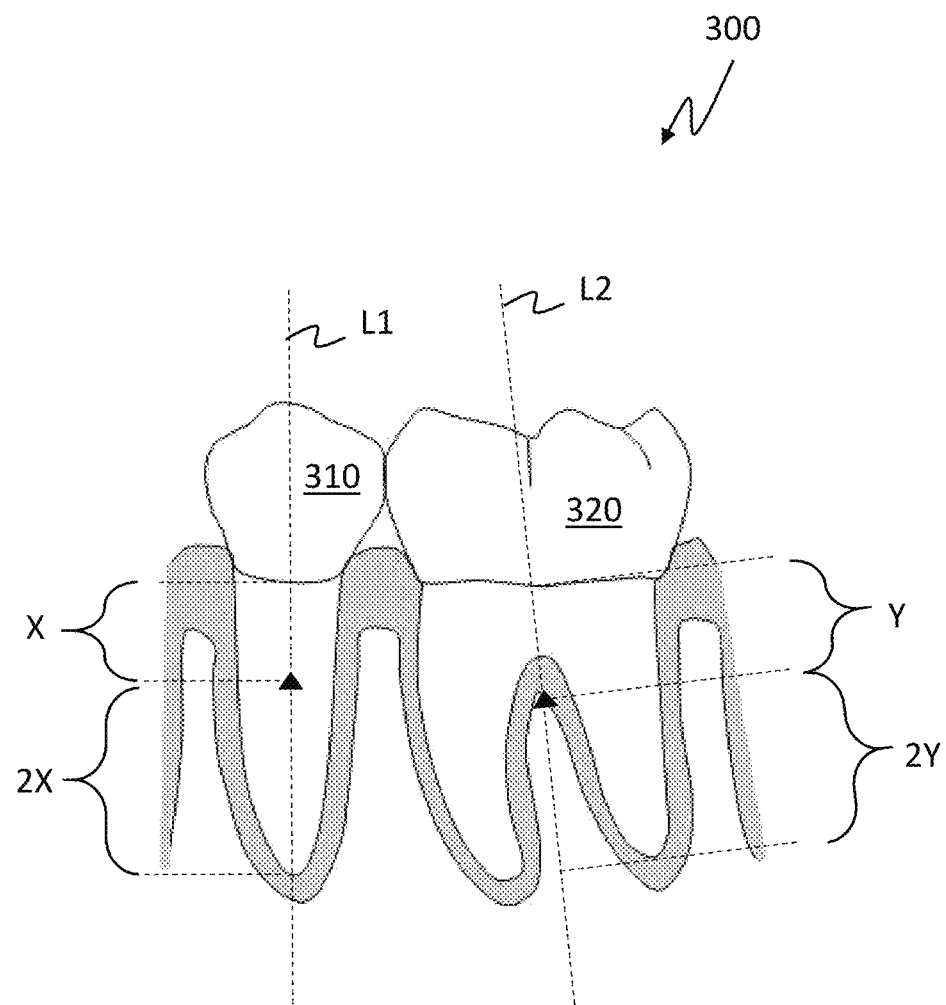
FIG. 3 is a schematic illustration depicting one variation of determining a center of rotation of a tooth in an integrated patient model.

For example, as shown in the schematic of FIG. 3, a longitudinal axis L1 (as projected onto the side view of FIG. 3) for a tooth 310 may be determined as extending generally between an apex of the root of tooth 310 and an upper surface of the crown of tooth 310. The center of rotation (denoted by the triangular marker) of tooth 310 may be estimated as located as between about one-third to about half, or about one-third of the length of the root of the tooth 310 measured in the apical direction (toward the apex of the root) along the longitudinal axis L1. In other words, the center of rotation is located about a distance X from the base of the root and a distance 2X from the apex of the root. As another example, as shown in the schematic of FIG. 3, a longitudinal axis L2 (as projected onto the side view of FIG. 3) for a tooth 320 may be determined as extending generally between a bottom central point of the tooth 320 and an upper central point of the tooth 320. Generally, the center of rotation (denoted by the triangular marker) of tooth 320 may be estimated as located at between about one third to about half, or about one-third of the length of the root of the tooth 320 measured in the apical direction (toward the apex of the root) along the longitudinal axis L2. In other words, the center of rotation is located about a distance Y from the base of the root and a distance 2Y from the apex of the root.

In some variations, the center of rotation (centroid) of the tooth may be automatically determined based on software-instructed analysis of the integrated patient model. For example, different anatomical regions (e.g., crown, root, periodontal ligament, bone, etc.) may be identified based on voxel density as described above. In view of such identification of these regions, total volume and overall shape of the tooth (including crown and root) may be automatically determined in the integrated patient model. Accordingly, the center of rotation may be automatically determined by analyzing the tooth volume as depicted in the integrated patient model.

Generally, in some variations, the determined center of rotation may be a center of resistance of the tooth root or portions thereof. The center of resistance may be defined as a point where a single force for which the line of action passing through the center of resistance produces tooth translation in the direction of the line of action of the applied force.

Figure 10A:
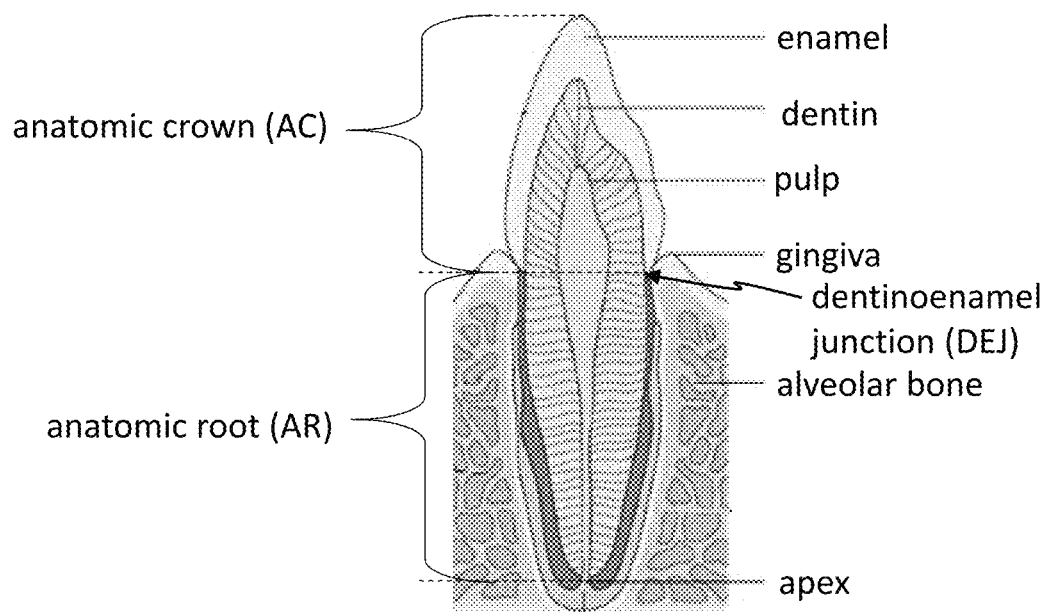
FIG. 10A is an illustrative schematic depicting a tooth and its anatomical root.
Figure 10B:
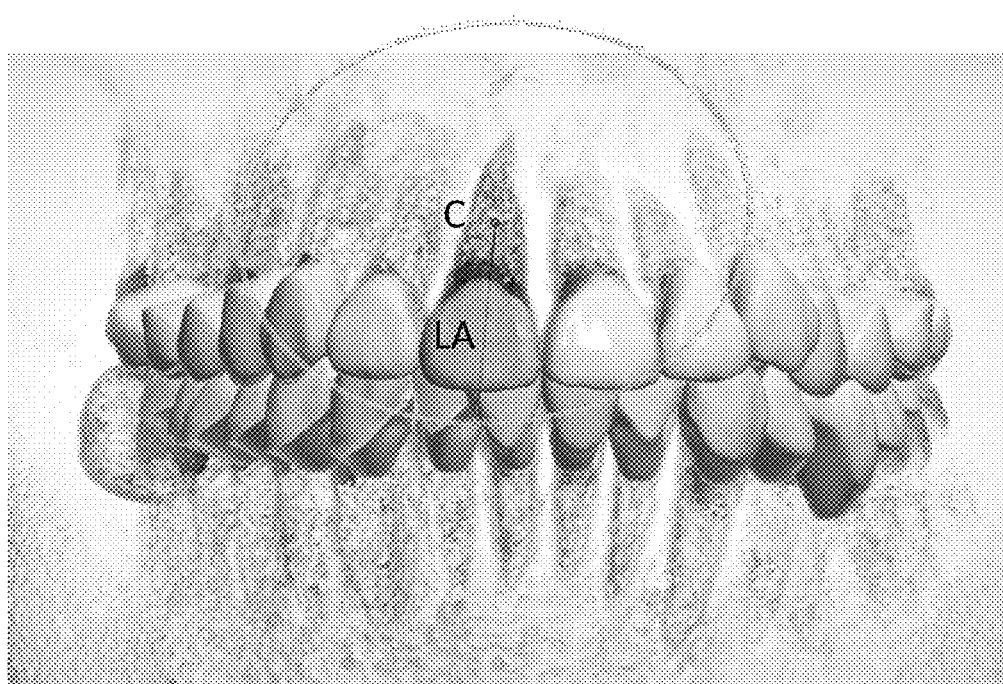
FIG. 10B is an illustrative schematic depicting a center of resistance of a tooth determined based on its anatomical root.

In one variation, the center of rotation of a tooth is determined based on a calculated center of resistance of the anatomical root of the tooth. As shown in FIG. 10A, the anatomical root (AR) of the tooth extends from where the crown meets the root at the dentinoenamel junction (DEJ) to the tooth root apex. Voxel data for the anatomical root is provided by the volumetric scan of the patient (separately or in the integrated patient model). In these variations, the center of resistance of the tooth is between about ⅓ and about ½ the distance along the longitudinal axis of the anatomical root from the DEJ to the root apex. This is related to the calculation of the centroid of a cone and the calculation of the centroid of a cylinder, since the root morphology of a tooth tapers unevenly toward the apex (somewhat between a cone and a cylinder). FIG. 10B illustrates the determination of an exemplary center of resistance (C) along a longitudinal axis (LA) based on the anatomical root extending from the DEJ.

Figure 11A:
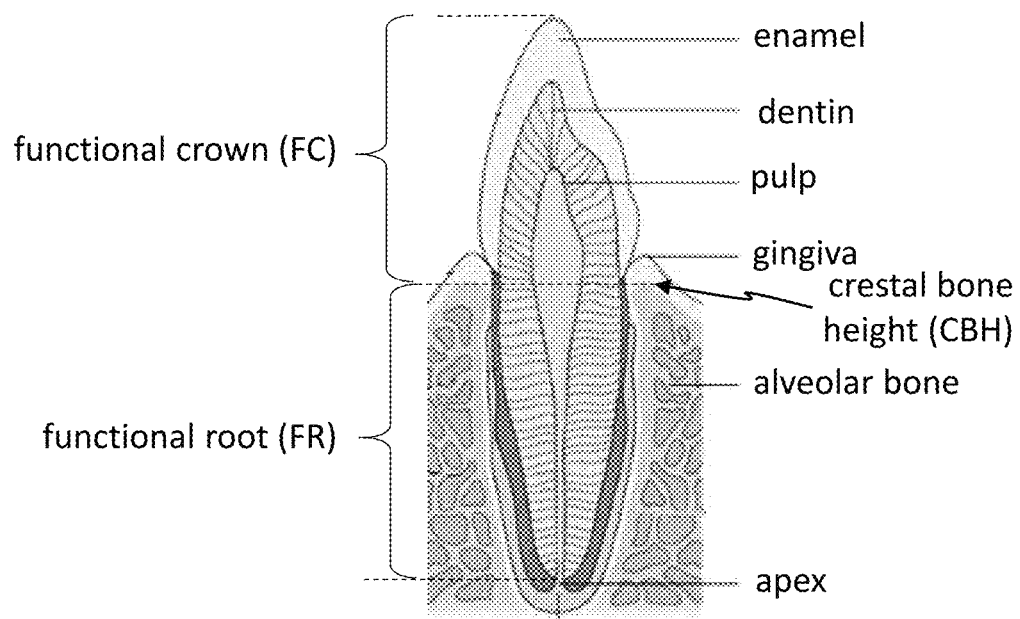
FIG. 11A is an illustrative schematic depicting a normal tooth and its functional root.
Figure 11B:
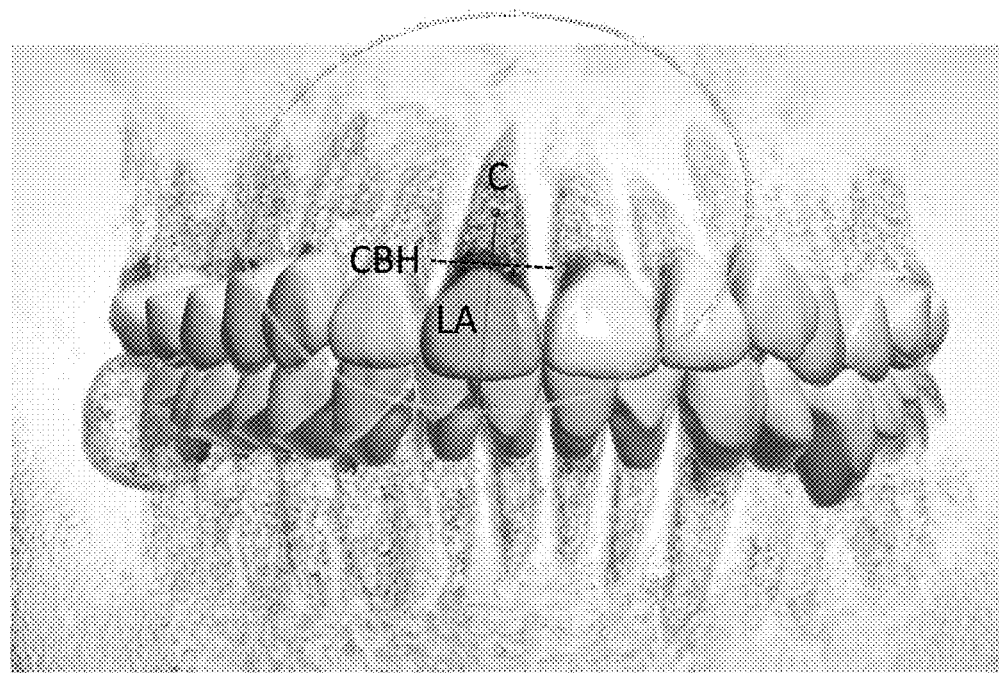
FIG. 11B is an illustrative schematic depicting a center of resistance of a tooth determined based on its functional root.
Figure 11C:
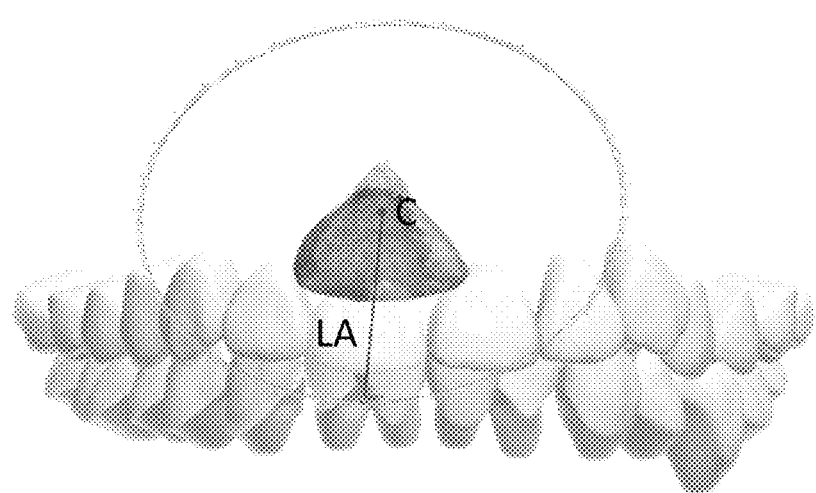
FIG. 11C is a projected view of a tooth that is inclined in a predicted rotation as the result of forces applied to the tooth, in movement around the center of resistance shown in FIG. 11B.

In another variation, the center of rotation of a tooth is determined based on a calculated center of resistance of the functional root of the tooth. As shown in the schematic of a healthy ("normal") tooth depicted in FIG. 11A, the functional root (FR) is a smaller portion of the anatomical root (AR in FIG. 10A) of the tooth that extends from the crestal bone height (CBH) to the tooth root apex, or equivalently, the length of the root that is surrounded by bone (some "non-functional" portion of the anatomical root may extend above the crest of the crest of the surrounding bone). The functional root may alternatively be defined as the volume of root which has a contacting surface of periodontal ligament directly to surrounding bone. In this variation, the center of resistance of the functional root is between about ⅓ and about ½ the distance of the functional root from the base of the functional root to the root apex. For example, FIG. 11B illustrates the determination of an exemplary center of resistance (C) along a longitudinal axis (LA) based on the functional root. Specifically, the center of resistance (C) is located at about ⅓ of the distance along the longitudinal axis (LA) between the crestal bone height (CBH) shown in dotted line and the apex of the root. Accordingly, upon application of forces during orthodontic treatment on the tooth, the tooth is expected to move around the center of resistance (C). For example, FIG. 11C illustrates a projected view of a tooth that is inclined (crown tilted anteriorly, root tilted posteriorly) in a predicted rotation around the center of resistance (C) as the result of forces applied to the tooth.

Figure 12A:
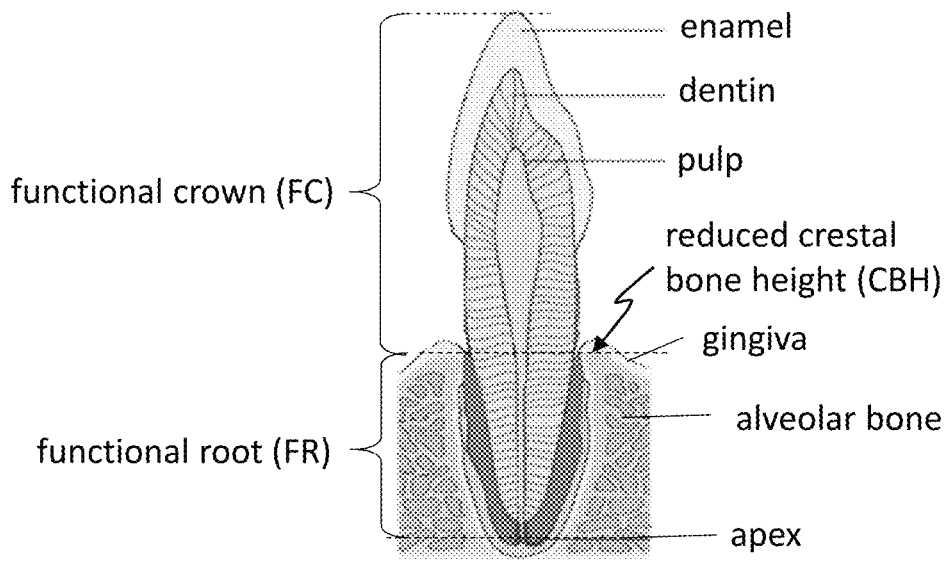
FIG. 12A is an illustrative schematic depicting an abnormal tooth and its functional root.
Figure 12B:
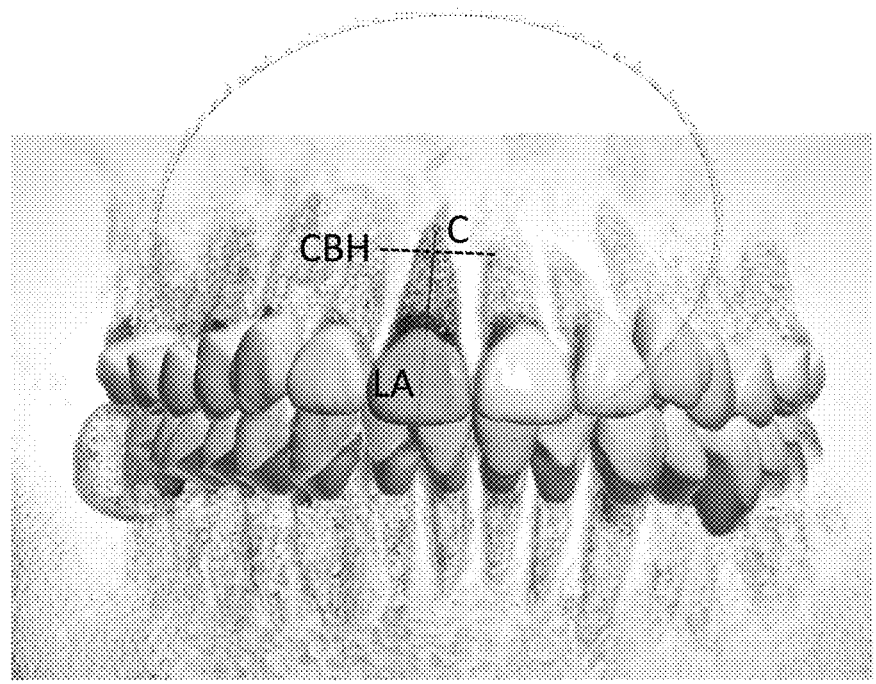
FIG. 12B is an illustrative schematic depicting a center of resistance of a tooth determined based on its functional rate.
Figure 12C:
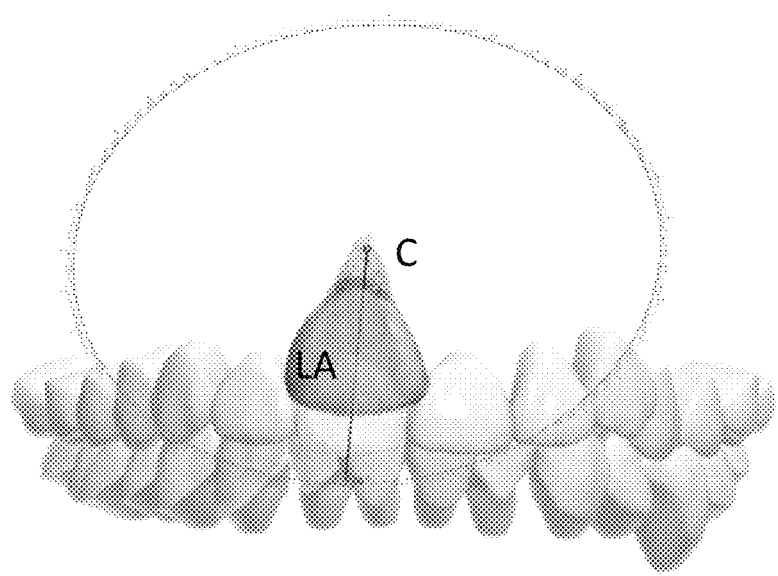
FIG. 12C is a projected view of a tooth that is inclined in a predicted rotation as the result of forces applied to the tooth, in movement around the center of resistance shown in FIG. 12B.

In some instances, the functional root may be substantially different in length than the anatomical root, such as for an unhealthy or abnormal tooth. Thus, in some variations, use of the functional root, rather than the anatomical root, for determining center of resistance (as center of rotation) may be more accurate. For example, FIG. 12A is an illustrative schematic of a tooth that is surrounded with a crestal bone having a reduced height. Due to the reduced crestal bone height (CBH) and receded gingiva, there is a significant portion of anatomical root (between the functional crown (FC) and the gingiva) that is exposed. Since the functional root is associated with the actual portion of the root that is restrained by the crestal bone, a determination of center of rotation using the functional root may be more likely to be representative of the tooth's movement physics, compared to a determination of center of rotation using the anatomical root. For example, FIG. 12B illustrates the determination of an exemplary center of resistance (C) along a longitudinal axis (LA) based on the functional root. Specifically, the center of resistance (C) is located at about ⅓ of the distance along the longitudinal axis (LA) between the reduced crestal bone height (CBH) shown in dotted line and the apex of the root. Accordingly, upon application of forces during orthodontic treatment on the tooth, the tooth is expected to move around the center of resistance (C). For example, FIG. 12C illustrates a projected view of a tooth that is inclined (crown tilted anteriorly, root tilted posteriorly) in a predicted rotation around the center of resistance (C) as the result of forces applied to the tooth. This predicted movement based on a determination using functional root may be more likely to be more accurate than a similar predicted movement based on a determination using anatomical root.

Figure 13:
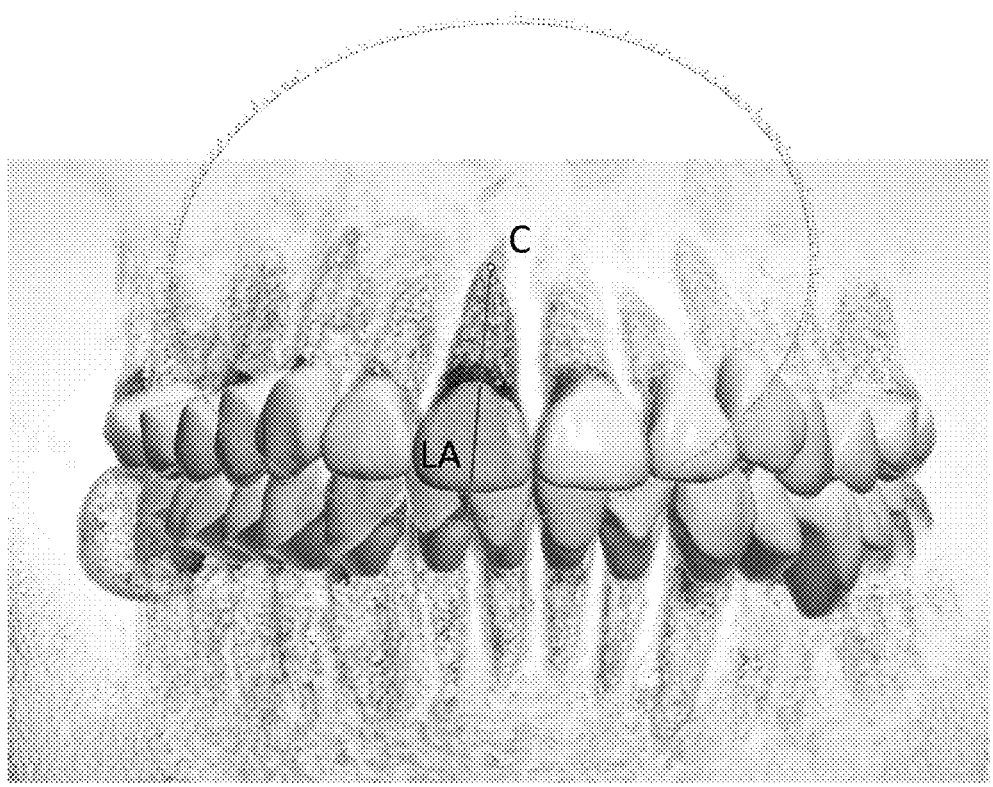
FIG. 13 is an illustrative schematic depicting a user-selected center of resistance of a tooth.

In other variations, the user may manually select (e.g., place a marker, or otherwise indicate) a center of rotation (e.g., based on visual inspection). For example, as shown in FIG. 13, the user may manually select a center of rotation of a tooth as a user-selected location, which may located be some preferred distance from (or coinciding with) the root apex along the longitudinal axis of the tooth.

The voxel density of the volumetric data for bone surrounding teeth can be greater or lesser, as a reflection of the patient's bone being more or less dense. Accordingly, the density of the voxel data for the surrounding bone may influence the magnitude and/or direction of the forces necessary to move a tooth, and/or may affect the limits of tooth movement within the alveolar or cortical bone of the patient's jaw. Accordingly, the center of rotation of a tooth may be at least partially based on the voxel density corresponding to bone surrounding the tooth.

Any one of the above-described variations of determining a center of rotation of a tooth may be automatically executed, or presented to a user (e.g., within a software application) as options for selection. Furthermore, in some variations, two or more of the above-described variations of determining a center of rotation of a tooth may be performed, and their results may be averaged to generate an averaged center of rotation for the tooth. Additionally or alternatively, any one or more of the above-described variations of determining a center of rotation of a tooth may be performed, and the resulting location may be manually adjusted (e.g., up or down along the longitudinal axis of the tooth) by the user if desired.

Patient Facial Phenotyping

One variable that tends to influence the complexity of orthodontic treatment is the facial phenotype of the patient. There are two extreme phenotypes that diverge in opposite ways from normal: brachycephalic and dolichocephalic. These two phenotypes can be identified by the degree and direction which a skull (namely, the viscerocranium of the skull) develops. These qualities can be calculated directly and/or inferred from morphologic features within the volumetric scan data of a patient. These phenotypes influence the magnitude and direction of forces applied to teeth for tooth movement during orthodontic treatment, and the design of orthodontic devices. For example, facial phenotype data may influence how teeth must move in order to correct or mask divergence from normal dental relationships. In other words, the same dental relationship may require different treatment if the patient is brachycephalic rather than dolichocephalic, or vice versa.

Skulls of brachycephalic individuals are characterized by a shorter and wider face. Additional features generally include stronger jaw musculature, denser jaw bones, increased biting forces, and characteristic occlusal relationships such as a deep bite. These individuals tend to have hypodivergent mandibles which are angled differently than normal in relation to the skull. Consequences of this facial pattern on the teeth include increased complexity of orthodontic treatment, greater difficulty of treatment, and increased risk of wear between the upper and lower incisors. Accordingly in some variations, the orthodontic treatment planning methods and systems such as those described herein may be used to provide for more accurate and efficient orthodontic treatments for brachycephalic individuals.

The skulls of dolichocephalic individuals are characterized by a longer, narrower face. Additional features include weaker jaw musculature, less dense bones, decreased biting forces, and characteristic occlusal relationships such as an open bite. These individuals tend to have hyperdivergent mandibles which are angled differently than normal in relation to the skull. This facial pattern may be associated with nasal airway obstruction during facial development. Consequences of this facial pattern on the teeth include increased complexity of orthodontic treatment, greater difficulty of treatment, and increased risk of wear between the upper and lower posterior teeth. Accordingly in some variations, the orthodontic treatment planning methods and systems such as those described herein may be used to provide for more accurate and efficient orthodontic treatments for dolichocephalic individuals.

Treatment Planning

As described herein, utilizing the integrated patient model (as a combination of intraoral surface scan data and volumetric scan data) enables greater accuracy in identifying the true center of rotation of a tooth for a patient, thereby improving accuracy of orthodontic treatment planning and reducing overall orthodontic treatment times compared to conventional treatment planning methods using, for example, only intraoral surface scan data. For example, a longitudinal axis of a tooth may be determined based solely on intraoral surface scan data (e.g., identifying a longitudinal line that roughly divides the surface appearance of the tooth in half in at least two planes), and a center of rotation along the longitudinal axis may be identified for treatment planning purposes. However, intraoral surface scan data fails to capture variations in crown and root morphology of a tooth. Accordingly, such a longitudinal axis for a tooth (and the center of rotation determined based on the longitudinal axis) will tend to be inaccurate, thereby leading to less effective treatment. In contrast, as described herein, a longitudinal axis of a tooth may be determined based on an integrated patient model incorporating both intraoral surface scan data and volumetric scan data. Such a longitudinal axis for a tooth (and center of rotation determined based on the longitudinal axis) will tend to be more accurate, thereby leading to more effective and efficient treatment. Accordingly, in some variations the methods described herein may include generating a suitable treatment plan based at least in part on the determined center of rotation(s) of one or more teeth.

In some variations, treatment planning may include generating a series of one or more aligner trays with tooth-receiving cavities, each aligner tray corresponding to a respective tooth arrangement such that a patient wearing the series of aligner trays in a particular sequential order (e.g., one tray per one week, two weeks, three weeks, or other suitable period of time) experiences a gradual transition of their dentition from an original tooth arrangement to a desired or targeted tooth arrangement. The forms of the aligner trays may correspond to different stages that gradually move each of one or more teeth around a respective center of rotation determined as described above. For example, each aligner tray may to a respective tooth arrangement such that the series of aligner trays progressively move teeth in treatment paths in accordance with their centers of rotation for natural movement. The aligner trays may, for example, be formed from rigid or semi-rigid polymer (e.g., through vacuum forming, injection molding, 3D printing, etc.). The aligner trays may be provided to a patient individually (e.g., shipped one at a time according to predetermined intervals) or in one or more sets.

Figure 14:
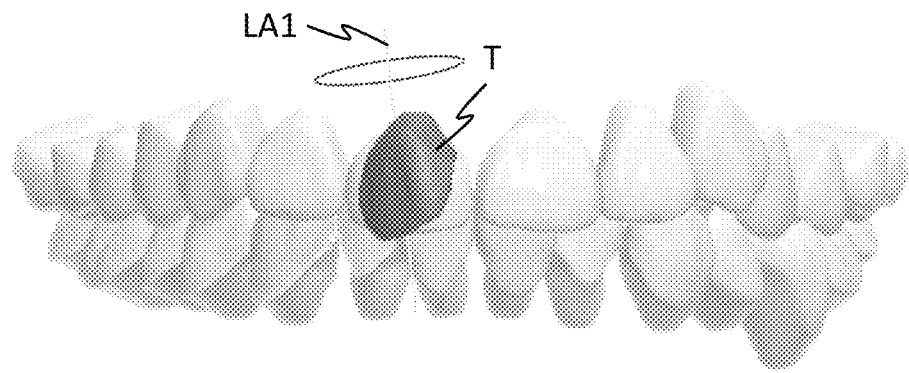
FIG. 14 depicts an exemplary tooth's longitudinal axis and planned rotation generated based on analysis of solely intraoral surface scan data.
Figure 15:
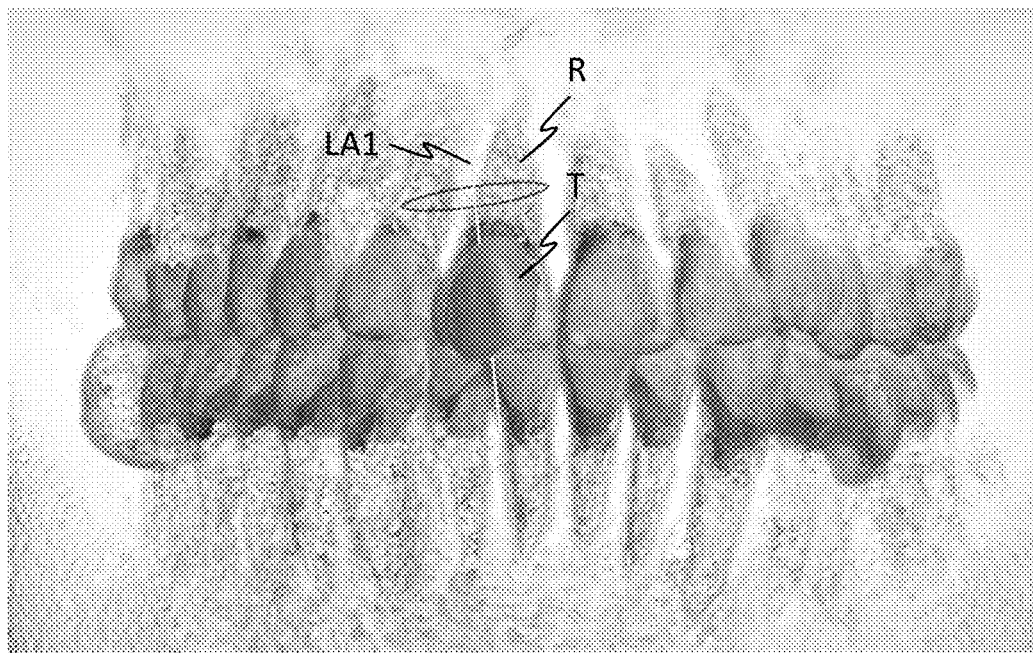
FIG. 15 depicts the exemplary tooth's longitudinal axis and planned rotation in FIG. 16, overlaid over a volumetric scan image.

FIG. 14 depicts an exemplary model corresponding to intraoral surface scan data for a patient's dentition. The surface scan information was analyzed to determine a longitudinal axis (LA1) passing through an incisor (T). As shown in FIG. 14, a treatment plan for the patient involves the incisor (T) undergoing a 50-degree rotation around the longitudinal axis (LA1). However, as shown in FIG. 15 depicting a volumetric scan image for the patient's dentition, the longitudinal axis (LA1) is substantially angularly offset from the general axis of the root (R) of the incisor (T), indicating that the determined longitudinal axis (LA1) is inaccurate or incorrect for the incisor (T).

Figure 16:
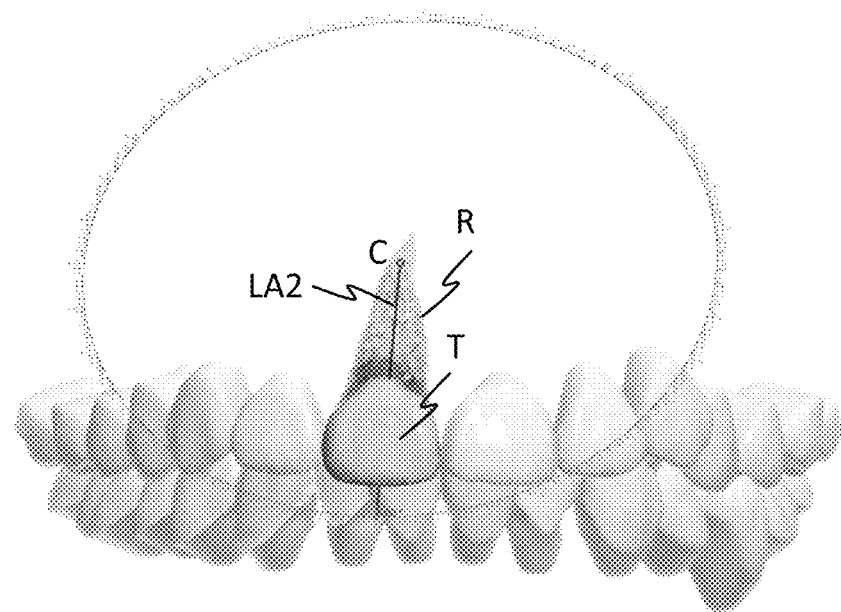
FIG. 16 depicts an exemplary tooth's longitudinal axis based on analysis of an integrated patient model including intraoral surface scan data and volumetric scan data.
Figure 17:
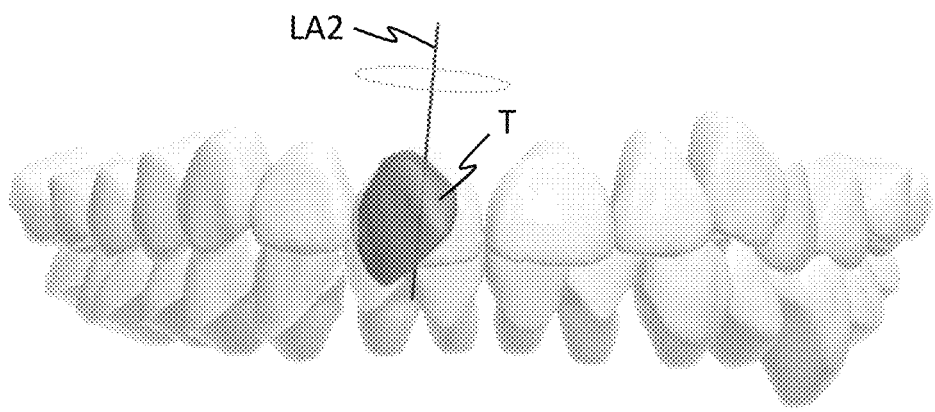
FIG. 17 depicts the exemplary tooth's longitudinal axis and planned rotation as shown in FIG. 18.

In contrast, FIG. 16 depicts an exemplary partial integrated patient model that overlays an intraoral surface scan image and a volumetric scan image for the patient's dentition. Specifically, FIG. 16 depicts a partial integrated patient model including a surface scan image of the incisor (T) and a portion of the volumetric scan image depicting the root (R) of the incisor (T). The integrated patient model was analyzed to determine a longitudinal axis (LA2) passing through the incisor (T) and along the root (R). A center of rotation (center of resistance (C)) was selected at a ⅓ distance along the longitudinal axis (LA2) from a reduced crestal height to the apex of the root (similar to that described above with reference to FIGS. 12A-12C). FIG. 17 depicts a treatment stage for the patient that involves the incisor (T) undergoing a 50-degree rotation around the longitudinal axis (LA2).

Figures 18A, 18B:
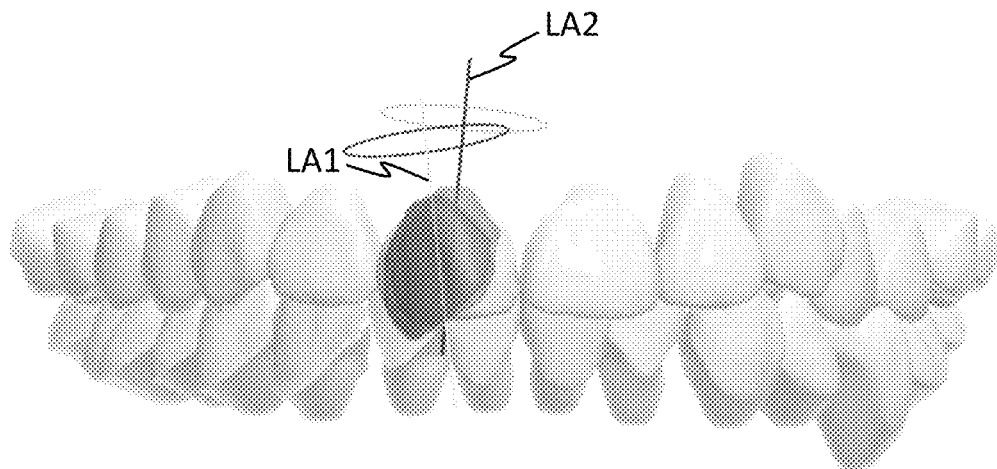
FIG. 18A depicts an overlay of the exemplary tooth's longitudinal axes and planned rotation as shown in FIGS. 14 and 17.
FIG. 18B is a table summarizing error in the longitudinal axis determined as shown in FIGS. 14 and 15.

Since the longitudinal axes (and centers of rotation) for incisor (T) are different in the treatment planning methods associated with FIG. 14 (intraoral surface scan only) and FIG. 16 (integrated patient model incorporating both an intraoral surface scan and a volumetric scan), the rotational path of the incisor (T) around these different axes and centers of rotation are also different. FIG. 18A depicts an overlay of the rotations of the incisor (T) depicted in FIGS. 14 and 17, and illustrates the relative inaccuracy of the longitudinal axis (LA1), compared to the longitudinal axis (LA2). Additionally, FIG. 18B summarizes the notable error in the longitudinal axis (LA1) (which is correlated to error in determined center of rotation) that is based on only intraoral surface scan data. As shown in the table of FIG. 18B, use of only the intraoral surface scan resulted in determination of a longitudinal axis (LA1) having an approximately 12.42-degree error in faciolingual inclination, an approximately 11.56-degree error in mesiodistal angulation, and an approximately 47.29-degree error in rotation. Furthermore, use of only the intraoral surface scan resulted in determination of a longitudinal axis (LA1) having translational errors as measured from the center of rotation in LA2 as an origin, including approximately 2.95 mm left/right error, approximately 3.17 mm forward/backward error, and approximately 0.64 mm extrusion/intrusion error.

Systems for Orthodontic Treatment Planning

FIG. 2 illustrates various components of an exemplary system for orthodontic treatment planning. Specifically, an exemplary system may include a general computing device 230 including one or more processors 240, one or more memory devices 250, one or more network communication devices 260, one or more output devices 270, and/or one or more user interfaces 280. Exemplary general computing devices include a desktop computer, laptop computer, and mobile computing devices (e.g., tablets, mobile phones).

The processor 240 may be any suitable processing device configured to run and/or execute a set of instructions or code, and may include one or more data processors, image processors, graphics processing units, physics processing units, digital signal processors, and/or central processing units. The processor may be, for example, a general purpose processor, a Field Programmable Gate Array (FPGA), an Application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types (e.g., MOSFET technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some variations, the memory 250 may include a database and may be, for example, a random access memory (RAM), a memory buffer, a hard drive, an erasable programmable read-only memory (EPROM), an electrically erasable read-only memory (EEPROM), a read-only memory (ROM), Flash memory, and the like. The memory may store instructions to cause the processor to execute modules, processes, and/or functions such as scan data processing and alignment. In some variations, the memory 250 may receive intraoral surface scan data 212 and/or volumetric scan data 222 in full (e.g., DICOM files generated by scanner-specific software). Additionally or alternatively, the memory 250 may receive intraoral surface scan data 212 and/or volumetric scan data 222 in parts, such as in a real-time or near real-time feed of data directly from the intraoral scanner 210 and/or volumetric scanner 220.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CDROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Furthermore, one or more network communication devices 260 may be configured to connect the general computing device to another system (e.g., intraoral scanner 210, volumetric scanner 220, Internet, remote server, database, etc.) by wired or wireless connection. In some variations, the general computing device may be in communication with one or more other general computing devices via one or more wired or wireless networks. In some variations, the communication device may include a radiofrequency receiver, transmitter, and/or optical (e.g., infrared) receiver and transmitter configured to communicate with one or more device and/or networks. In an exemplary variation, the network communication devices 260 may include a cellular modem (e.g., 3G/4G cellular modem) such that it is advantageously not dependent on internet Wireless Fidelity (WiFi) access for connectivity.

Alternatively, wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, WiFi, voice over Internet Protocol (VoIP), or any other suitable communication protocol. In some variations, the devices herein may directly communicate with each other without transmitting data through a network (e.g., through NFC, Bluetooth, WiFi, RFID, and the like). For example, devices (e.g., one or more computing devices, an intraoral scanner 210, and/or a volumetric scanner 220, etc.) may directly communicate with each other in pairwise connection (1:1 relationship), or in a hub-spoke or broadcasting connection ("one to many" or 1:m relationship). As another example, the devices (e.g., one or more computing devices and/or intraoral scanner 210, and/or volumetric scanner 220, etc.)

may communicate with each other through mesh networking connections (e.g., "many to many", or m:m relationships), such as through Bluetooth mesh networking.

As described above, the computing device in the system may include one or more output devices 270 such a display and/or audio device for interfacing with a user. For example, an output device may include a display that permits a user to view the integrated patient model, treatment planning steps, and/or other suitable information related to diagnosis and/or treatment planning for orthodontic treatment. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display. In some variations, an audio device may comprise at least one of a speaker, piezoelectric audio device, magnetostrictive speaker, and/or digital speaker.

The computing device may further include one or more user interfaces 280. In some variations, the user interface may comprise an input device (e.g., touch screen) and output device (e.g., display device) and be configured to receive input data. Input data may include, for example, a selection of image scan data (e.g., for rotation, cross-sectional viewing, segmenting and/or other suitable manipulation), a selection or placement of markers (e.g., to facilitate registration of surface scan data and volumetric scan data and/or facilitate model segmentation as described above) and/or other interaction with a user interface. For example, user control of an input device (e.g., keyboard, buttons, touch screen) may be received by the user interface and may then be processed by the processor and memory. Some variations of an input device may comprise at least one switch configured to generate a control signal. For example, an input device may comprise a touch surface for a user to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio data and recognize a user voice as a control signal.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method of orthodontic treatment planning for a patient, the method comprising:
receiving intraoral surface scan data of a dentition of the patient;
receiving volumetric scan data of the dentition;
combining the intraoral surface scan data and the volumetric scan data to generate an integrated patient model comprising at least one tooth; and
identifying one or more anatomical features of the integrated patient model based at least in part on voxel density.

2. The method of claim 1, wherein the one or more anatomical features comprise one or more of a root of the least one tooth, a crown of the at least one tooth, gingiva surrounding the at least one tooth, periodontal ligaments associated with the at least one tooth, and bone surrounding the at least one tooth.

3. The method of claim 1, wherein the identifying comprises comparing a voxel density of the at least one tooth with a predetermined threshold voxel density for the at least one tooth.

4. The method of claim 1, wherein the identifying comprises determining a first voxel density of the at least one tooth in the integrated patient model.

5. The method of claim 4, wherein the identifying further comprises determining a second voxel density of the one or more anatomical features and comparing the difference between the first and second voxel densities to a predetermined threshold difference.

6. The method of claim 1, wherein the orthodontic treatment comprises generating a plurality of aligner trays with tooth-receiving cavities, each aligner tray corresponding to a respective tooth arrangement.

7. A method of orthodontic treatment planning for a patient, the method comprising:
receiving intraoral surface scan data of a dentition of the patient;
receiving volumetric scan data of the dentition;
combining the intraoral surface scan data and the volumetric scan data to generate an integrated patient model comprising a root of at least one tooth; and
automatically separating the root of the at least one tooth from a remainder of the integrated patient model by identifying the root as a discrete volume.

8. The method of claim 7, wherein the remainder of the integrated patient model comprises one or more of a crown of the at least one tooth, gingiva surrounding the at least one tooth, periodontal ligaments associated with the at least one tooth, and bone surrounding the at least one tooth.

9. The method of claim 7, wherein the separating is based at least in part on voxel density of the root of the at least one tooth and the remainder of the integrated patient model.

10. The method of claim 7 further comprising defining, in the integrated model, a center of rotation of the root as a point located a predetermined distance from a base of the root to an apex of the root along a longitudinal axis of the at least one tooth.

11. The method of claim 7, wherein the root is the anatomical root of the at least one tooth.

12. The method of claim 7, wherein the root is the functional root of the at least one tooth.

13. The method of claim 7, wherein the intraoral surface scan data comprises optical color scan data, and wherein the volumetric scan data comprises CBCT X-ray scan data.

14. A method of orthodontic treatment planning for a patient, the method comprising:
receiving intraoral surface scan data of a dentition of the patient;
receiving volumetric scan data of the dentition;
combining the intraoral surface scan data and the volumetric scan data to generate an integrated patient model comprising at least one tooth; and
comparing, via the integrated patient model, a voxel density of the at least one tooth with a predetermined threshold voxel density for the at least one tooth.

15. The method of claim 14, wherein the integrated patient model comprises one or more anatomical features of the patient.

16. The method of claim 15, wherein the one or more anatomical features comprise one or more of a root of the at least one tooth, a crown of the at least one tooth, gingiva surrounding the at least one tooth, periodontal ligaments associated with the at least one tooth, and bone surrounding the at least one tooth.

17. The method of claim 16, wherein the root is the anatomical root of the at least one tooth.

18. The method of claim 16, wherein the root is the functional root of the at least one tooth.

19. The method of claim 15 further comprising defining, in the integrated model, a center of rotation of the at least one tooth as a point located a predetermined distance from a base of a root of the at least one tooth to an apex of the root along a longitudinal axis of the at least one tooth.

20. The method of claim 19, wherein the predetermined distance is between about one-third and about one-half of a distance from the base of the root to the apex of the root.

* * * * *